US007842721B2

(12) United States Patent
Lin et al.

(10) Patent No.: US 7,842,721 B2
(45) Date of Patent: Nov. 30, 2010

(54) COMPOSITION FOR TREATING CANCER CELLS AND SYNTHETIC METHOD FOR THE SAME

(75) Inventors: An-Shen Lin, Kaohsiung (TW); Yang-Chang Wu, Kaohsiung (TW); Kuo-Hsiung Lee, Kaohsiung (TW); Fang-Rong Chang, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 509 days.

(21) Appl. No.: 11/844,752

(22) Filed: Aug. 24, 2007

(65) Prior Publication Data

US 2009/0054516 A1   Feb. 26, 2009

(51) Int. Cl.
*A01N 43/16* (2006.01)
*C07D 311/92* (2006.01)

(52) U.S. Cl. .................. 514/455; 549/389; 549/392; 549/403; 514/457

(58) Field of Classification Search .................. 549/389, 549/392, 403; 514/455, 457
See application file for complete search history.

(56) References Cited

U.S. PATENT DOCUMENTS 6,340,694 B1   1/2002  Joo et al.
2007/0104804 A1   5/2007  Wu et al.

FOREIGN PATENT DOCUMENTS

TW   200718427 A   5/2007

OTHER PUBLICATIONS

Chang et al, DN 143:572675 abstract (2005).*
Nikolic et al DN 141:133508 abstract (2004).*
Lin, AS; Chang, FR; Wu, CC, et al. "New Cytotoxic Flavonoids from Thelypteris torresiana" Planta Med 2005; 71: 867-870.
Felpin et al. "Oxidation of 4-arylphenol trimethylsilyl ethers to p-arylquinols using hypervalent iodine(III) reagents" Tetrahedron Letters, Elsevier, Amsterdam, vol. 48, No. 3 Dec. 14, 2006, pp. 409-412.
Lin et al. "First Total Synthese 1,2,6-17 of Protoapigenone and its analogues as potent cytotoxic agents" Journal of Medicinal Chemistry Aug. 9, 2007, vol. 50, No. 16, pp. 3921-3927.
Chang et al. "Protoapigenone, a novel flavonoid, induces apoptosis in human prostate cancer cells through activation of p38 mitogen-activated protein kinase and c-Jun NH2-terminal kinase ½" Journal of Pharmacology and Experimental Therapeutics, Experimental Therapeutics vol. 325, No. 3, Jun. 1, 2008, pp. 841-849.
Shah et al. "Antitubercular properties of substituted hydroxycyclohexadienones" Letters in Drug Design and Discovery, Bentham Science Publishers, US vol. 3, No. 6, Jan. 1, 2006, pp. 419-423.

* cited by examiner

*Primary Examiner*—Janet L. Andres
*Assistant Examiner*—Raymond Covington
(74) *Attorney, Agent, or Firm*—Volpe and Koenig, P.C.

(57) ABSTRACT

A pharmaceutical composition having a cytotoxic effect to a cancer cell is provided. The pharmaceutical composition includes a flavonoid compound having a formula as

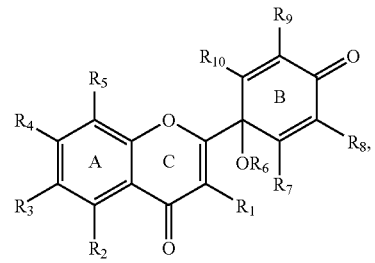

wherein B ring is a 4-oxo-cyclohexa-2,5-dienyl group, and any one of $R_1$-$R_{12}$ is one selected from a group consisting of hydrogen group, hydroxyl group, C1-C20 alkyl group, C1-C20 ether group, C1-C20 ester group, carboxyl group, halogen and sugar. The flavonoid compound is obtained from a chemical method being one of a total synthesis method and a semi-synthesis method.

17 Claims, 3 Drawing Sheets

COMPOSITION FOR TREATING CANCER CELLS AND SYNTHETIC METHOD FOR THE SAME

FIELD OF THE INVENTION

The present invention relates to a composition for treating cancer cells and a synthetic method therefor. More particularly, the method is total synthesis or semi-synthesis.

BACKGROUND OF THE INVENTION

Recently many extracts and their derivatives oriented from natural plants, such as vincristine, vinbalstine, camptothecin, taxol and its derivatives, palitaxel and docetaxel, have been widely used in clinical chemical therapy of a malignant tumor. Therefore, the effect of the extracts from natural plants has been a burgeoning research in the field of new drug development.

According to present publication, protoapegenone is a compound derived from *Thelypteris torresiana* produced in Taiwan. The compound has strong cytotoxic activities to many human cancer cell lines, including breast cancer cells (MCF-7, MDA-MB-231), liver cancer cells (Hep G2, and Hep 3B), and lung cancer cells (A549). (*Planta Medica* 71:867-870, 2005)

Prior to that, the protoapigenone can be obtained merely by extraction and isolation from natural plants. However, the efficiency of collecting the compound is under influence of unstable sources such as plant genes, humidity, and latitude, altitude of the collection location, season and individual variation of the plants.

In view of the above, the inventors develop a method for producing a compound for treating cancer cells through total synthesis or semi-synthesis based on the inventors' experience in studying the ingredient of natural plants and chemical synthesis for a long time. By using such preparation, the protoapigenone can be produced from commercially available chemical products without extracting from natural plants. Moreover, the activity of the synthetic compound has no obvious difference with nature product through a comparison of activity. Moreover, the source of the compound would be stable and preparation time would be saved. Further, yield of the compound can be estimated in a large scale production by using the synthetic method of the present invention.

Besides, many derivatives of protoapigenone will be produced from different initiators, reagents and intermediator. Moreover, the acidity, the alkalinity, the lipid solubility, the solubility, the activity and the toxicity of the compound can be changed by substituting with different functional groups so that a more potent compound with cytotoxic effect can be afforded. The summary of the present invention is described below.

SUMMARY OF THE INVENTION

It is an aspect of the present invention to provide a pharmaceutical composition having a cytotoxic effect to a cancer cell. The pharmaceutical composition comprises a flavonoid compound having at least one of the following formulas:

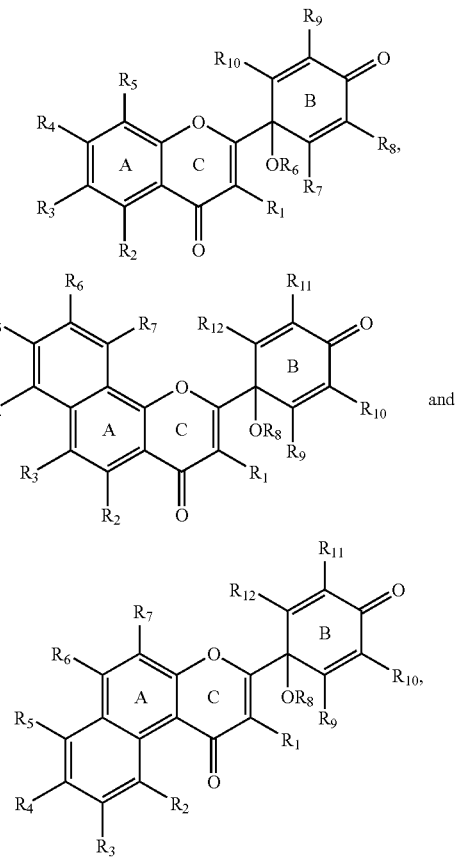

wherein B ring is a 4-oxo-cyclobexa-2,5-dienyl group, and any one of $R_1$-$R_{12}$ is one selected from a group consisting of hydrogen group, hydroxyl group, C1-C20 alkyl group, C1-C20 ether group, C1-C20 ester group, carboxyl group, halogen and sugar. In one preferred embodiment of this invention, flavonoid compound is obtained from a total synthesis method. In another preferred embodiment, the flavonoid compound is obtained from a semi-synthesis method.

Preferably, the pharmaceutical composition is used for treating a disease of a mammal.

Preferably, the disease is a cancer.

Preferably, the mammal is a human.

It is another aspect of the present invention to provide a method for synthesizing a specific flavonoid compound. The method comprises steps of mixing an acetophenone comprising a first protecting group with a benzaldehyde comprising a second protecting group to obtain a first compound through a Claisen-Schmidt Condensation reaction, reacting the first compound with a first catalyzer to obtain a second compound, removing the second protecting group from the second compound to obtain a third compound, reacting the third compound with a second catalyzer and an iodobenzene compound to obtain a fourth compound through an oxidation, and adding an acid into the fourth compound to remove the first protecting group and obtain the flavonoid compound. In a specific embodiment, the specific flavonoid compound is protoapigenone.

Preferably, the first protecting group is a MOM.

Preferably, the second protecting group is a benzyloxy group.

Preferably, the first catalyzer is an iodine.

Preferably, the second catalyzer is a TEMPO.

Preferably, the iodobenzene compound is one of an iodobenzene diacetate and a [bis(trifluoroacetoxy)iodo]benzene.

Preferably, the acid is a hydrochloric acid.

It is a further aspect of the present invention to provide a method for synthesizing a specific flavonoid compound. The method comprises steps of providing a flavonoid compound comprising a 4'-hydroxy group, and mixing the flavonoid compound with a first catalyzer and an iodobenzene compound to obtain the specific flavonoid compound. In an exemplary embodiment, the specific flavonoid compound is derivatives of protoapigenone.

Preferably, the first catalyzer is a TEMPO.

Preferably, the iodobenzene compound is one of an iodobenzene diacetate and an [bis(trifluoroacetoxy)iodo]benzene.

Other objects, advantages and efficacies of the present invention will be described in detail below taken from the preferred embodiments with reference to the accompanying drawings, in which:

DETAILED DESCRIPTION OF THE PREFERRED EMBODIMENT

I. Definitions

Figure 1:
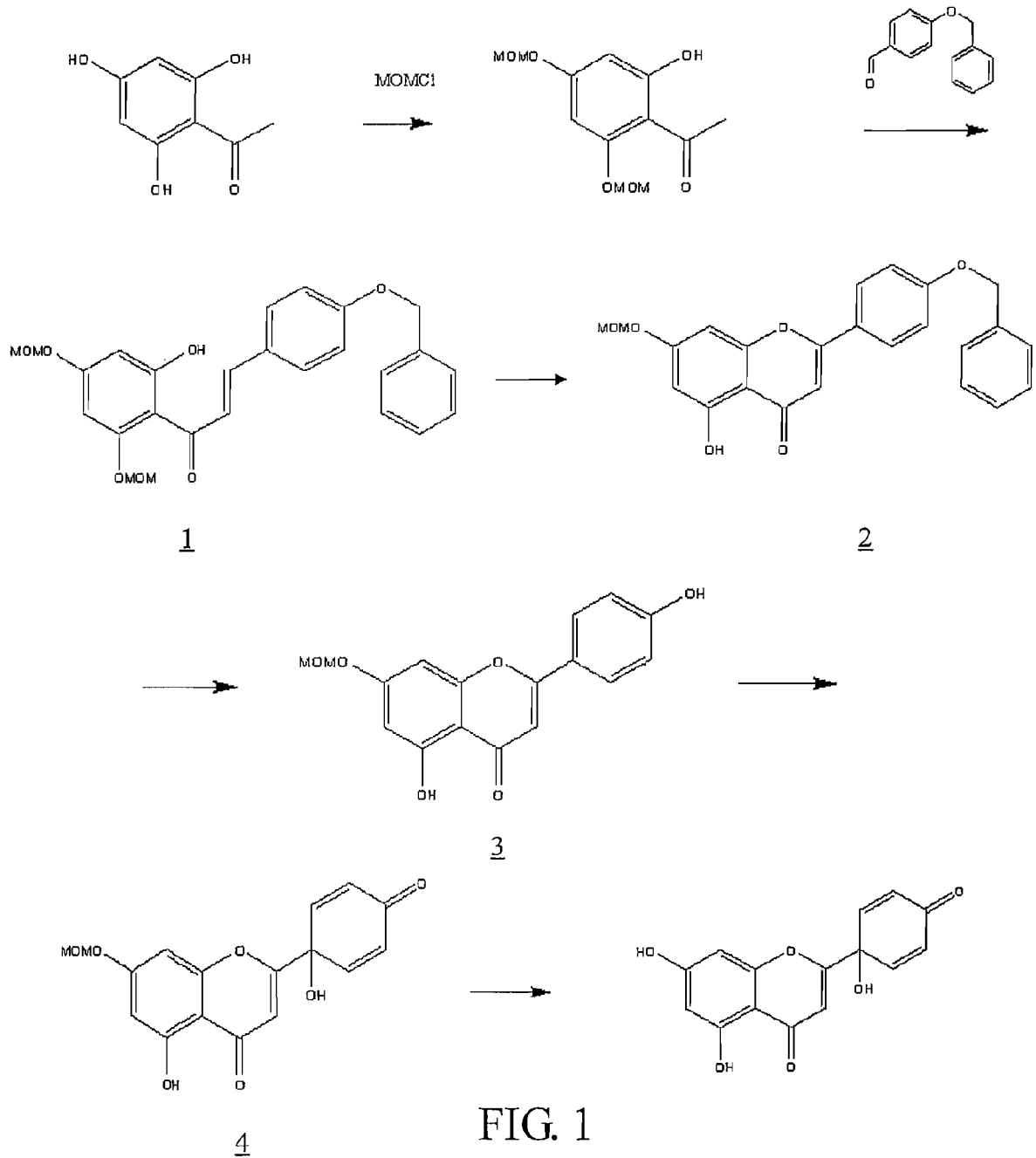
FIG. 1 is a flow chart showing the total synthesis method for preparing the flavonoid compound in the present invention.

The following definitions are provided in order to aid understanding of the detailed description of the present invention:

As used herein, the term "C1-C20 alkyl" represents a straight- or branched-chain saturated hydrocarbon containing 1 to 20 carbon atoms which may be unsubstituted or substituted by one or more substituents. Examples of C1-C20 alkyl groups include methyl, ethyl, propyl, 2-propyl, n-butyl, isobutyl, tert-butyl, pentyl, and the like. Similarly, the term "C1-C20 ether" and "C1-C20 ester" represents a compound containing 1 to 20 carbon atoms which may be unsubstituted or substituted by one or more substituents.

As used herein, the term "alkyl" represents both straight and branched, saturated and unsaturated hydrocarbon groups.

As used herein, the term "ether" represents any of a number of organic compounds whose molecules contain two hydrocarbon groups joined by single bonds to an oxygen atom.

As used herein, the term "ester" refers to and covers any compound falling within the definition of that term as classically used in organic chemistry. It includes organic and inorganic esters, where A is —COOH; this term covers the products derived from treatment of the function with alcohols or thioalcohols. The ester is derived from compounds where A is —$CH_2$ OH; this term covers compounds derived from organic acids capable of forming esters such as phosphorous-based and sulfur-based acids, or compounds of the formula —$CH_2$ OCOR where R is any substituted or unsubstituted aliphatic, aromatic, heteroaromatic or aliphatic-aromatic group.

The term "halogen" refers to fluorine, chlorine, bromine or iodine.

The term "total synthetisis" refers to the chemically synthetic method using starting materials other than one of the naturally occurring compounds. The term "semi-synthesis" refers to the chemical synthetic method using naturally occurring compounds as starting materials.

As used herein, the term "mammal" refers to the Mammalia class of higher vertebrates, especially human.

The term "protecting" as used herein refers to a process in which a functional group in a chemical compound is selectively masked by a non-reactive functional group in order to allow a selective reaction(s) to occur elsewhere on the chemical compound. Such non-reactive functional groups are herein termed as "protecting groups." Such groups are generally able to be selectively introduced and removed using mild reaction conditions that do not interfere with other portions of the subject compounds.

The term "oxidation" refers to the loss of one or more electrons in an element, compound, or chemical substituent/subunit. In an oxidation reaction, electrons are lost by atoms of the element(s) involved in the reaction. The charge on these atoms must then become more positive. The electrons are lost from the species undergoing oxidation and thus electrons appear as products in an oxidation reaction.

The term "protoapigenone" used in the embodiment refers to a flavonoid compound containing a 4'-oxocyclohexa-2',5'-dienyl moiety rather than a 4'-hydroxycyclohexa-2',5'-dienyl moiety in a nature product. Except the particularly mentioned "natural protoapigenone" or "protoapigenone extracted from a plant", the term "protoapigenone" mentioned in the embodiment represents the flavonoid derived from a chemical synthesis method.

II. Detailed Description

Example I

The Total Synthetic Method for Preparing Protoapigenone Compound

Please refer to FIG. 1, which is a flowchart showing a total synthesis method for preparing the flavonoid compound in the present invention. Firstly, an exceed amount (for example, 7E (equivalent)) of potassium carbonate is added into an acetone solution containing 2',4',6'-Trihydroxy-acetophenone monohydrate to form a first mixture, and the first mixture is stirred. Then, 3E of chloromethyl methyl ether is added dropwise into the first mixture. For fully reacting, the first mixture is refluxed for 90 minutes. After cooling, the first mixture is filtrated to obtain a precipitation. The precipitation is rinsed with acetone and chloroform, and then evaporated and purified by column chromatography on a silica gel (isocratic elution, 90% n-hexane/10% ethyl acetate) to obtain a 2'-hydroxy-4'-6'-dimethoxymethyl-acetophenone with MOM protecting groups on the 4' and the 6' positions in 50.3% yield.

Subsequently, the aforementioned 2'-hydroxy-4'-6'-dimethoxymethyl-acetophenone and a 4-benzyloxy-benaldehyde are mixed to carry out a Claisen-Schmidt Condensation reaction. In this condensation reaction, 2'-hydroxy-4'-6'-dimethoxymethyl-acetophenone and 2E of 4-benzyloxy-benaldehyde are mixed in ethanol solution to obtain a second mixture. After stirring the second mixture, a catalytic amount of potassium hydroxide is added thereinto. The second mixture is stirred at room temperature for 30 hrs, and then the solvent was evaporated under reduced pressure. The concentrated second mixture is chromatographed on a silica gel and eluted with n-hexane/ethyl acetate to obtain a first compound in 87.2% yield.

0.2E of iodine is added into a proper amount of pyridine solution containing the dissolved first compound. After the pyridine solution is heated and refluxed for 5 hrs, a sodium thiosulfate is added thereinto. The pyridine solution is extracted with ethyl acetate/water and then purified by a column chromatography on silica gel to obtain a second compound in 85.5% yield.

Then, the second compound is dissolved in an ethyl acetate/methanol solution. 1E of 10% palladium carbon (Pd/C) is added into the ethyl acetate/methanol solution and the solution mixture is stirred under an atmosphere of hydrogen for 3 hrs. After a filtration process for removing the palladium carbon, the above solution is concentrated under reduced pressure to obtain a third compound in 88.9% yield.

An oxidation reaction is carried out by reacting the third compound with 1E of iodobenzene diacetate or [bis(trifluoroacetoxy)iodo]benzene in the presence of a catalytic amount of TEMPO under a heating condition to obtain a reactant a. The reactant a is extracted with ethyl acetate/water and then isolated repeatedly on a silica gel column to obtain a forth compound in 22.2% yield.

The MOM protecting groups on the 4' and the 6' positions of the forth compound is removed by heating with hydrochloric acid to provide a protoapigenone compound in 46.7% yield.

Example II

The Semi-Synthesis Method for Preparing Derivatives of Protoapigenone

The embodiment herein illustrates a semi-synthesis method for synthesizing the following compounds: compound 8a: protoflavonone (IIUPAC name is 2-(1-hydroxy-4-oxocyclohexa-2,5-dienyl)-4H-chromen-4-one), compound 10a: 5-hydroxyprotoflavone (IIPAC name is 2-(1-hydroxy-4-oxocyclohexa-2,5-dienyl)-5-hydroxy-4H-chromen-4-one), compound 15a: β-naphthoflavonone (IIPAC name is 3-(1-hydroxy-4-oxocyclohexa-2,5-dienyl)-1H-benzo[f]chromen-1-one) and compound 18a: 5-hydroxy-7-methoxyprotoflavonone (IIPAC name is 5-hydroxy-2-(1-hydroxy-4-oxocyclohexa-2,5-dienyl)-7-methoxy-4H-chromen-4-one).

Figure 2:
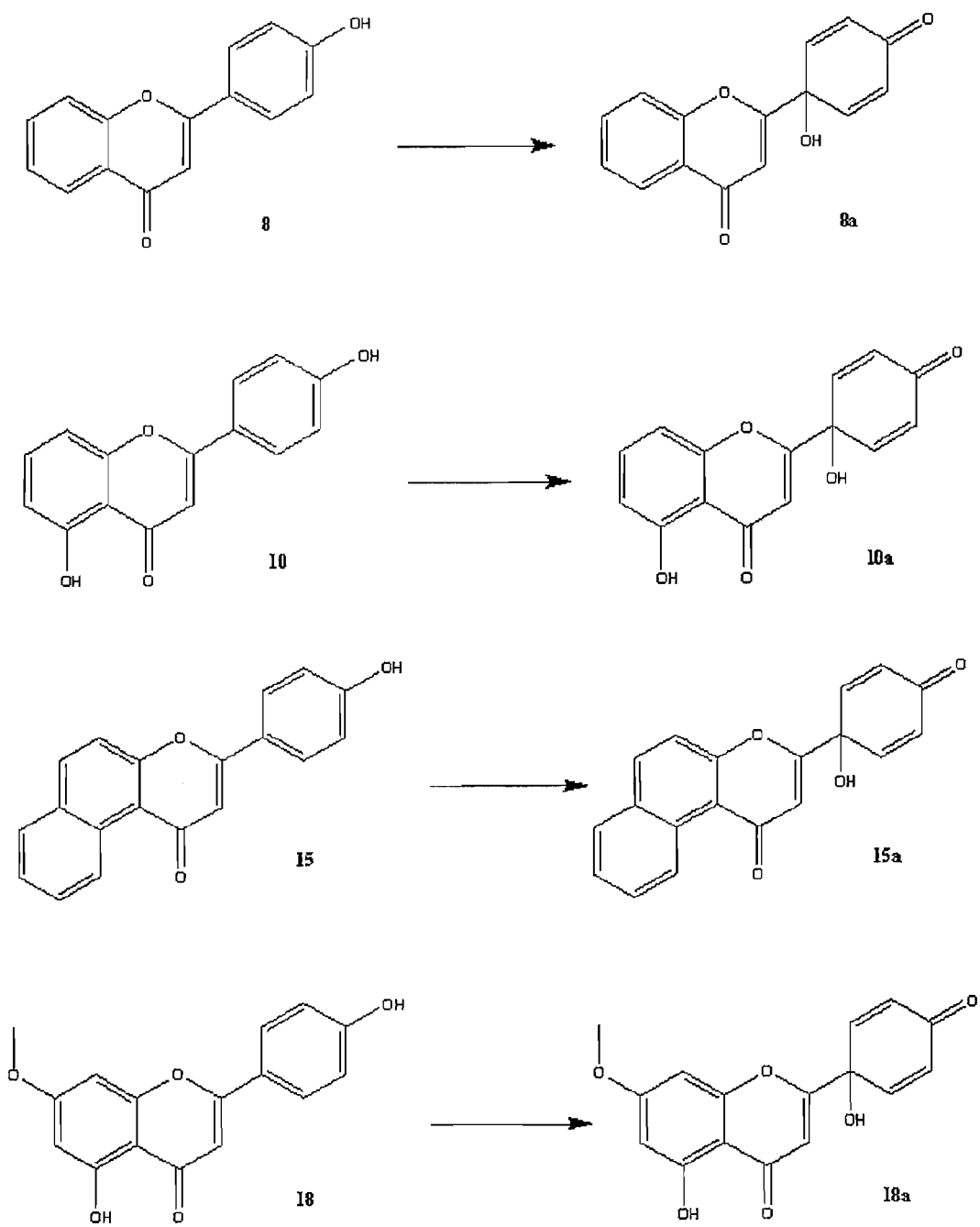
FIG. 2 shows chemical structures of compounds 8a, 10a, 15a and 18a prepared by a semi-synthesis method in the present invention.

Firstly, a commercially available precursor flavonoid such as 4'-hydroxyflavone, 4'-5-dihydroxyflavone, 4'-hydroxy-β-naphthoflavone and 4'-5-dihydroxy-7-methoxyflavone is selected as a starting material and dissolved in an appropriate amount of water. Secondly, a catalytic amount of TEMPO is added to the precursor flavonoid. The solution mixture is oxidized with 1E of iodobenzene diacetate or [bis(trifluoroacetoxy)iodo]benzene in a heating condition to obtain a product b. Sequentially, the product b is extracted with ethyl acetate/water to afford an organic layer, and the organic layer is isolated by chromatography repeatedly to obtain the compound 8a, compound 10a, compound 15a and compound 18a in 20-30% yield. The structural changes of these compounds are shown in FIG. 2.

Figure 3:
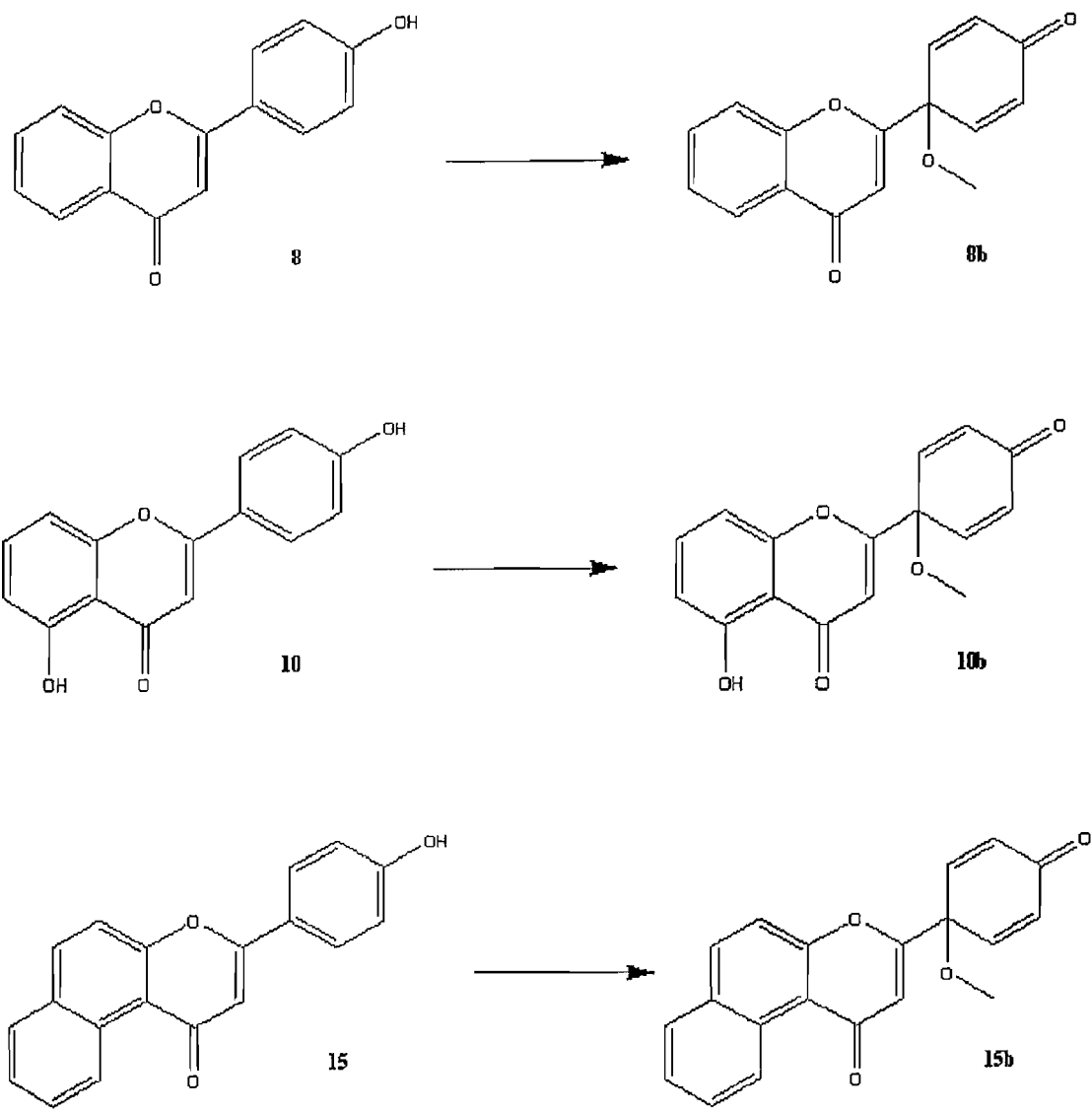
FIG. 3 shows chemical structures of compounds 8b, 10b, and 15b prepared by a semi-synthesis method in the present invention.

In another way, the above precursor flavonoids can be dissolved in an appropriate amount of methanol. A catalytic amount of TEMPO is added to the precursor flavonoid respectively. The solution mixture is oxidized with 1E of iodobenzene diacetate or [bis(trifluoroacetoxy)iodo]benzene in a heating condition to obtain a product c. Similarly, the product c is extracted with ethyl acetate/water to afford an organic layer, and the organic layer is isolated by chromatography repeatedly to obtain a compound having a methoxy group on the 1'-position such as 1'-methoxyprotoflavonoen (compound 8b), 1'-methoxy-5-methylprotoflavonone (compound 10b), and 1'-methoxy-β-naphthoflavone (compound 15b) in 25-35% yield. The structural changes of these compounds are shown in FIG. 3.

Example III

The Bio-Activities of the Derivatives of Protoapigenone

Cells Culture

Human liver (HepG2 and Hep3B), breast (MCF-7 and MDA-MB-231), and lung (A549) cancer cell lines were propagated in RPMI-1640 medium supplement with 10% (v/v) FBS, 100 U/mL penicillin and 100 g/mL streptomycin at 37° C. in a humidified atmosphere of 5% $CO_2$ and 95% air. The culturing medium is changed every three days. Upon confluency, cells were subcultured to confluency, and used for experiments. The experimental period is determined according to the aim of experiment.

Cytotoxicity Assay

Cytotoxicity is measured by the MTT calorimetric method. Cells were seeded at densities of 5,000-10,000 cells/well in 96-well tissue culture plates. On day two, cells are treated with test compounds for another 72 hrs. After drug treatment, attached cells were incubated with MTT (0.5 mg/mL) for 1 hr and subsequently solubilized in DMSO. The absorbency at 550 nm is then measured using a microplate reader. The result of cell viability is shown in Table 1. The IC50 is the concentration of agent that reduces the cell viability by 50% under the experimental conditions, and the cytotoxic compound, Doxorubicin, is used as a positive control.

TABLE 1

| Compound | $IC_{50}$ (μg/mL) | | | | |
|---|---|---|---|---|---|
| | HepG2 | Hep3B | MDA-MB-231 | MCF-7 | A549 |
| protoapigenone | 2.32 | 0.65 | 0.41 | 1.07 | 3.96 |
| 8a | 1.71 | 0.32 | 0.18 | 0.44 | 1.33 |
| 8b | 10.95 | 1.45 | 1.47 | 2.14 | >20 |
| 10a | 1.34 | 0.35 | 0.18 | 0.93 | 1.37 |
| 10b | 7.64 | 0.66 | 0.54 | 1.55 | 16.36 |
| 15a | 1.08 | 0.09 | 0.12 | 0.20 | 0.55 |
| 15b | 3.16 | 0.35 | 0.37 | 0.86 | 8.20 |
| 18a | 0.17 | 0.20 | 0.13 | 0.51 | 0.93 |
| Doxorubicin | 0.29 | 0.36 | 0.08 | 0.43 | 0.21 |

As shown in Table 1, each test compound is examined for in vitro cytotoxic activities against several human cancer lines and compared with the related flavonoid protoapigenone and doxorubicin, a positive control. Remarkably, compounds 8a, 10a, 15a and 18a show significant cytotoxic activity with notable $IC_{50}$ against cancer cell lines, especially Hep3B and MDA-MB-231. It is known that both the protoapigenone compound and its derivatives synthesized by a chemical method have cytotoxic effect against cancer cells, similar to nature protoapigenone compound extracted from a plant. Among the derivatives, compound 18a shows the highest potency against all five cancer cell lines. Amazingly, this compound also exhibits significantly enhanced activity against the HepG2 human liver cancer cell line, while most analogs show comparatively weak activity against this cell line. From the above data, it is proved that many derivatives having more potency to particular cancer cells than protoapigenone can be produced by using the synthetic method of the present invention.

To summarize, the present invention provides a composition having a cytotoxic effect to a cancer cell and a method for synthesizing the same. The total synthesis or semi-synthesis method can generate the cytotoxic compound protoapigenone. Further, the method of the present invention can produce other derivatives with similar activity or even with better activity.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A pharmaceutical composition having a cytotoxic effect to a cancer cell comprising:
    a flavonoid compound having at least one of the following formulas:

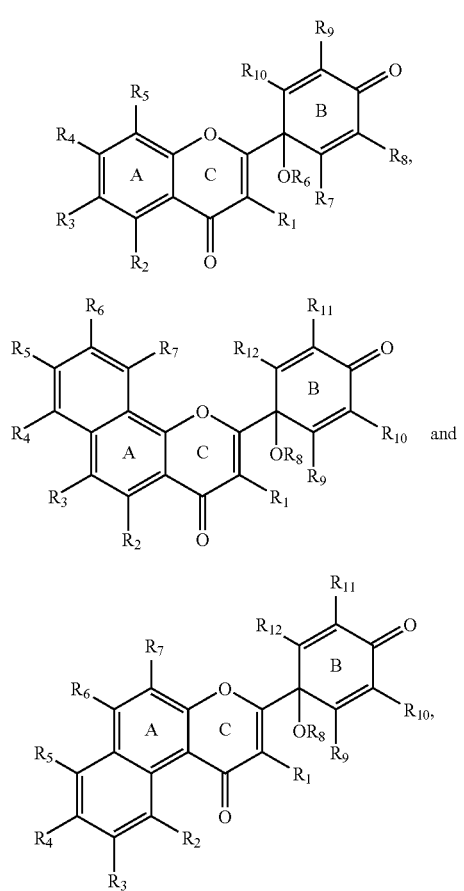

wherein:
    B ring is a 4-oxo-cyclohexa-2,5-dienyl group, and any one of $R_1$-$R_{12}$ is one selected from a group consisting of hydrogen group, hydroxyl group, C1-C20 alkyl group, C1-C20 ether group, C1-C20 ester group, carboxyl group, halogen and sugar;
    when $R_2$ of formula 1 is a hydroxyl group, $R_4$ of formula 1 is one selected from a group consisting of hydrogen group, C1-C20 alkyl group, C1-C20 ether group, C1-C20 ester group, carboxyl group, halogen and sugar; and
    when $R_4$ of formula 1 is a hydroxyl group, $R_2$ of formula 1 is one selected from a group consisting of hydrogen group, C1-C20 alkyl group, C1-C20 ether group, C1-C20 ester group, carboxyl group, halogen and sugar.

2. The composition as claimed in claim 1, wherein the flavonoid compound is obtained from a chemical method being one of a total synthesis method and a semi-synthesis method.

3. A method comprising administering to a mammal in need thereof a therapeutically effective amount of the pharmaceutical composition of claim 1.

4. The method as claimed in claim 3, wherein the disease is a cancer.

5. The method as claimed in claim 4, wherein the mammal is a human.

6. A synthesis method for synthesizing a flavonoid compound of claim 1 comprising steps of:
    mixing an acetophenone comprising a first protecting group with a benzaldehyde comprising a second protecting group to obtain a first compound through a Claisen-Schmidt Condensation reaction;
    reacting the first compound with a first catalyzer to obtain a second compound;
    removing the second protecting group from the second compound to obtain a third compound;
    reacting the third compound with a second catalyzer and an iodobenzene compound to obtain a fourth compound through an oxidation; and
    adding an acid into the fourth compound to remove the first protecting group and obtain the flavonoid compound.

7. The method as claimed in claim 6, wherein the first protecting group is a MOM.

8. The method as claimed in claim 6, wherein the second protecting group is a benzyloxy group.

9. The method as claimed in claim 6, wherein the first catalyzer is an iodine.

10. The method as claimed in claim 6, wherein the second catalyzer is a TEMPO.

11. The method as claimed in claim 6, wherein the iodobenzene compound is one of an iodobenzene diacetate or a [bis(trifluoroacetoxy)iodo]benzene.

12. The method as claimed in claim 6, wherein the acid is a hydrochloric acid.

13. A synthesis method for synthesizing a flavonoid compound of claim 1 comprising steps of:
    mixing an acetophenone comprising a first protecting group with a benzaldehyde comprising a second protecting group to obtain a first compound through a Claisen-Schmidt Condensation reaction;
    reacting the first compound with a first catalyzer to obtain a second compound;
    removing the second protecting group from the second compound to obtain a third compound;
    reacting the third compound with a second catalyzer and an iodobenzene compound to obtain a fourth compound through an oxidation; and adding an acid into the fourth compound to remove the first protecting group and obtain the flavonoid of claim 1.

14. A synthesis method for synthesizing a specific flavonoid compound comprising steps of:
   providing a flavonoid compound comprising a 4'-hydroxy group; and
   mixing the flavonoid compound with a first catalyzer and an iodobenzene compound to obtain the specific flavonoid compound.

15. The method as claimed in claim 14, wherein the first catalyzer is a TEMPO.

16. The method as claimed in claim 14, wherein the iodobenzene compound is one of an iodobenzene diacetate or an [bis(trifluoroacetoxy)iodo]benzene.

17. A synthesis method for synthesizing a specific flavonoid compound comprising steps of:
   providing a flavonoid compound comprising a 4'-hydroxy group; and
   mixing the flavonoid compound with a first catalyzer and an iodobenzene compound to obtain the specific flavonoid compound, wherein the specific flavonoid compound is the flavonoid of claim 1.

* * * * *